United States Patent [19]

Park et al.

[11] Patent Number: 5,250,291

[45] Date of Patent: Oct. 5, 1993

[54] COSMETIC PRODUCT

[75] Inventors: Andrew C. Park, Wirral, United Kingdom; Allan R. Burger, Passaic, N.J.

[73] Assignee: Chesebrough-Pond's USA Co., Division of Conopco, Inc., Greenwich, Conn.

[21] Appl. No.: 426,476

[22] Filed: Oct. 23, 1989

Related U.S. Application Data

[63] Continuation of Ser. No. 129,640, Dec. 7, 1987, abandoned.

[30] Foreign Application Priority Data

Dec. 23, 1986 [GB] United Kingdom ............... 8630724

[51] Int. Cl.$^5$ .................... A61K 7/32; A61K 7/34; A61K 7/36; A61K 7/38
[52] U.S. Cl. ................. 424/66; 424/DIG. 5; 424/47; 424/67; 424/68
[58] Field of Search ............... 424/65, 66, 68, DIG. 5

[56] References Cited

U.S. PATENT DOCUMENTS 4,346,079  8/1982  Roehl ..................... 424/DIG. 5

FOREIGN PATENT DOCUMENTS 1068215  12/1979  Canada ..................... 424/68
004355   1/1980   Japan ...................... 424/68

Primary Examiner—Dale R. Ore
Attorney, Agent, or Firm—Milton L. Honig

[57] ABSTRACT

A solid antiperspirant product, such as a stick, suitable for topical application to the skin comprises an antiperspirant agent in the form of fine particles dispersed in a solid matrix. The matrix comprises anhydrous ethanol, anhydrous isopropanol or a mixture thereof, an hydrophobically-treated clay as a suspending agent, a gelling agent and other antiperspirant adjuncts as required. The weight ratio of the suspending agent to the anhydrous alcohol is from 1:3 to 1:15 to achieve maximum efficacy as measured by sweat weight reduction following topical application of the product to perspiring skin.

16 Claims, No Drawings

COSMETIC PRODUCT

This is a continuation application of Ser. No. 129,640, filed Dec. 7, 1987, now abandoned.

FIELD OF INVENTION

The invention relates to antiperspirant products, particularly to antiperspirant stick products of the type comprising a finely divided antiperspirant agent dispersed in a solid matrix, which products have an exceptionally high efficacy in use. A particularly preferred embodiment of the invention is in the form of a stick of circular or oval cross-section contained in a stick dispenser. The invention is also concerned with a process for making these high efficacy antiperspirant products.

BACKGROUND AND PRIOR ART

For inhibiting perspiration, the application to the skin of many different antiperspirant active compounds has been described in the literature. However, those compounds most widely employed in commercial products of the stick type for this purpose are basic aluminium halides, especially aluminium chlorohydrate which has an aluminium/chlorine molar ratio of about 2, and aluminium zirconium chlorohydrate complexes, including those combined with glycine, such as aluminium zirconium trichlorhydrex-GLY and aluminium zirconium tetrachlorhydrex-GLY. Especially popular are stick products in which the antiperspirant active is present as a powder in a finely divided form.

The effectiveness of an antiperspirant product can be assessed by subjecting human volunteers to thermal stress and gravimetric determination of axilla sweat.

By employing such a procedure, it can be shown that powder-containing stick antiperspirant products are more effective in reducing or eliminating the appearance of sweat at the skin surface than the so-called solution type antiperspirants, as the powder form allows for a greater amount of the antiperspirant active to be delivered to and deposited on the skin surface. Even so, powder antiperspirant products currently available on the market generally have limited efficacy in that a sweat reduction (as hereinafter defined) of no more than about 38% is achievable.

A further problem which can be experienced when using antiperspirant products of the powder-containing stick type is their tendency to be greasy and undesirably soft.

Just such a problem can occur with a powder-containing antiperspirant stick such as that described by Armour-Dial Inc. in their U.S. Pat. No. 4,126,679. This patent concerns a solid composition comprising 15 to 40% of an astringent metallic salt in powder form suspended in a matrix comprising 10 to 65% of volatile silicone and 15 to 70% of stearyl alcohol. Experience has shown, however, that this type of stick can be greasy and somewhat soft in use. Applicants have now discovered that by employing an anhydrous alcohol and a clay suspending agent with a much reduced level of volatile silicone, then a firmer, less greasy, stick is obtainable. Furthermore, the improved stick shows superior efficacy in use, in that sweat reduction (as hereinafter defined) of at least 45% is attainable.

DEFINITION OF THE INVENTION

According to the invention, there is provided a solid antiperspirant product suitable for topical application to the skin, which comprises from 5 to 35% by weight of an antiperspirant agent in the form of fine particles dispersed in a solid matrix comprising:
  (i) from 15 to 75% by weight of the product of a substantially anhydrous alcohol chosen from ethanol, isopropanol or a mixture thereof;
  (ii) from 2 to 15% by weight of the product of a suspending agent chosen from hydrophobically-treated clays;
  (iii) an effective amount of a gelling agent; and
  (iv) the balance of the matrix, if any, comprising antiperspirant adjuncts;
provided that the weight ratio of the suspending agent to the anhydrous alcohol is from 1:3 to 1:15.

DISCLOSURE OF THE INVENTION

The Antiperspirant Agent

The antiperspirant agent to be employed in the product according to the invention is in the form of a finely divided powder having a maximum particle diameter of not greater than $100\mu$, preferably no greater than $70\mu$ and preferably about $45\mu$. It is important not to exceed a maximum particle diameter of about $100\mu$ for this ingredient in order to obtain a uniform dispersion of the antiperspirant agent in the final solid product, thereby avoiding sedimentation or settling of this powder in the hot melt from which the solid antiperspirant product is obtained during the manufacturing process to be described later in this specification.

Examples of suitable antiperspirant agents are aluminium and/or zirconium salts, such as aluminium chloride; aluminium sulphate; aluminium chlorohydrate; basic aluminium bromide, zirconyl chloride; zirconyl hydroxide; zirconyl chlorohydrate; complexes of aluminium hydroxide, zirconyl chloride and aluminium chlorohydrate; complexes of aluminium hydroxide, zirconyl chlorohydrate, and aluminium chlorohydrate; complexes of dihydroxyaluminium glycinate, zirconyl chloride and/or zirconyl chlorohydrate and aluminium chlorohydrate; complexes of zirconyl chloride and/or zirconyl chlorohydrate and aluminium chlorohydrate; complexes of zirconyl chloride and/or zirconyl chlorohydrate with aluminium chlorohydrate and an amino acid, such as glycine; and mixtures of two or more of the above.

Preferred antiperspirant agents are those which have a high antiperspirant efficacy. One class of such materials are the aluminium zirconium chlorohydrate complexes. Examples are aluminium zirconium trichlorohydrate; aluminium zirconium tetrachlorohydrate and alumium zirconium pentachlorohydrate (these are CTFA generic names). These compounds may be combined with glycine to give for example the compounds known under the CTFA generic names aluminium zirconium trichlorohydrex-GLY and aluminium zirconium tetrachlorohydrex-GLY. Methods for preparing aluminium zirconium chlorohydrates are described in a number of patents, for example U.S. Pat. Nos. 4,028,390 (Armour) and 3,792,068 (Procter & Gamble) the disclosures of which are incorporated herein by reference. Suitable aluminium zirconium chlorohydrate powders for use in the antiperspirant compositions of this invention are available from the Reheis Chemical Company under the trade names REZAL 36GP and REZAL 67P (REZAL is trade mark) and from Wickhen Products Incorporated, under the trade names WICKENOL 369 and WICKENOL 379 and WICKENOL 373 (WICK- ENOL is a trade mark). Other preferred antiperspirant agents of high efficacy are the special active forms of basic aluminium chloride, such as activated aluminium chlorohydrate, which have a particular distribution of polymeric species in aqueous solution and obtainable by procedures described in U.S. Pat. No. 4,359,456 (Gosling et al). Similar processes for making highly active forms of aluminium chlorohydrate involving the ageing of aluminium chlorohydrate in an aqueous medium are described in British Patent Specification No. 2 144 992 (Gillette). The disclosures of the Gosling et al and Gillette patents are incorporated herein by reference.

Further examples of activated aluminium chlorohydrate which can be employed as the antiperspirant agent are available from Reheis under the trade name REACH. The antiperspirant agent may also be a urea or glycine complex of aluminium chlorohydrate prepared as described in European Patent No. 6738 (Unilever) and British Patent No. 1 597 497 (Unilever), respectively, the disclosure of which patents are incorporated herein by reference.

The amount of the antiperspirant agent employed in the product according to the invention is generally from 5 to 35%, preferably from 10 to 30%, and most preferably from 15 to 25% by weight of the product.

If an amount of less than 5% by weight of the antiperspirant agent is employed, then the efficacy of the product in use, expressed in terms of sweat reduction (as hereinafter defined), is likely to be poor. Also, if an amount of greater than 35% by weight of the antiperspirant active is employed, then deposition on the skin in use of an excessive amount of the antiperspirant active can leave an undesirable white deposit. Furthermore, the efficacy of the product in use is unlikely to be enhanced beyond that obtainable with products containing up to 35% by weight of the antiperspirant agent.

The Alcohol

The alcohol to be employed in the product according to the invention, which will form part of the solid matrix of the antiperspirant products, is an anhydrous alcohol chosen from ethanol, isopropanol and mixtures thereof. By "anhydrous" is meant that the alcohol should contain less than 1% by weight of water.

The amount of alcohol employed in the product according to the invention is from 15 to 75%, preferably from 20 to 50% by weight of the product.

If an amount of less than 15% by weight of the alcohol is employed, then the efficacy of the product expressed in terms of sweat reduction (as hereinafter defined) can be low. If an amount of greater than 75% by weight of the alcohol is employed, then the product is likely to be too soft in use and its efficacy in use can also be low.

The Suspending Agent

The suspending agent to be employed in the product according to the invention is chosen from hydrophobically treated clays. A preferred class of hydrophobically treated clays comprise smectite clays, examples of which include the montmorillonites, hectorites, and colloidal magnesium aluminium silicates.

Montmorillonite is colloidal, hydrated aluminium silicate obtained from bentonite of which it is the predominant constituent. A detailed discussion of bentonites can be found in the Kirk-Othmer Encyclopedia of Chemical Technology, 2nd Edition, Vol. 3 (1964) pp. 339–360, published by Interscience Publishers, which is incorporated herein by reference.

Hectorite, also a smectite clay, differs from montmorillonite in that there is almost a complete substitution of aluminium in the lattice structure of montmorillonite by magnesium and in addition, it contains lithium and fluorine.

The magnesium aluminium silicates are complexes of colloidal magnesium aluminium silicate richer in magnesium than aluminium. The hydrophobically treated magnesium aluminium silicates are commercially available under the name Veegum PRO from the R T Vanderbilt Co.

Preferred suspending agents for use in the product of the invention are hydrophobic clays available under the trade name of "Bentone". Bentones are prepared by reacting a suitable clay in a cation exchange system with an amine. Different amines are reacted to obtain a variety of Bentones, which may also differ in proportions of Si, MgO and $Al_2O_3$. Examples of useful "Bentone" suspending agents are "Bentone-27", which is a stearaluminium hectorite; "Bentone-34", which is quaternium 18 bentonite; "Bentone-38", which is quaternium 18 hectorite; and "Bentone-14" which is a clay-extended quaternium 18 hectorite, all of which have a particle size of below 5 microns and are commercially available from NL Industries Inc. Other suitable "Bentone" clays are Bentone SDI and Bentone SD2.

Yet further suitable clays are those hydrophobically treated smectite clays available under the trade names Perchem and Tixogel. Specific examples are Perchem clays 44, 97 and 108 and Tixogel VZ.

A further class of hydrophobically treated clays comprise hormite clays, an example of which is hydrophobically modified attapulgite clay available under the name Perchem DMA. Perchem clays are sold by Perchem Limited of Harlow, Essex, Great Britain, and Tixogel clays by Production Chemicals Limited of Stockport, Cheshire, Great Britain.

The amount of suspending agent employed in the product according to the invention is from 1 to 15%, preferably from 2 to 10% by weight of the product.

If an amount of less than 1% by weight of the suspending agent is employed, then the efficacy of the final product expressed in terms of sweat reduction (as hereinafter defined) can be low. If an amount greater than 15% by weight of the suspending agent is employed, then deposition on the skin of an excessive amount of the suspending agent can leave an undesirable white deposit. Furthermore, the efficacy of the product in use is unlikely to be enhanced beyond that obtainable with products containing up to 15% by weight of the suspending agent.

It is preferred that the weight ratio of the suspending agent to the anhydrous alcohol is from 1:3 to 1:15, preferably from 1:4 to 1:10.

The Gelling Agent

The gelling agent to be employed in the product according to the invention functions as the basic structural matrix of the stick composition and as an emollient.

Examples of gelling agents include low melting point waxes, having a melting point of from about 40° C. to 70° C., such as fatty acids and fatty alcohols containing from 8 to 22 carbon atoms, silicone waxes and glycerol monostearate. Preferred examples of such waxes include lauric acid, stearic acid, palmitic acid, cetyl alcohol, stearyl alcohol, myristyl alcohol and behenyl alcohol. The amount of the low melting point wax when employed will normally be from 8 to 35%, preferably 12 to 25% by weight of the product.

A quantity of water-insoluble high melting wax may also be incorporated in the antiperspirant stick composition to help provide the basic structure of the stick. Suitable waxes for this purpose are water-insoluble waxes, having a melting point of from about 70° C. to about 100° C. Examples of suitable waxes include; Castorwax MP80, Synchrowax HRC, carnaubau, beezwax spermaceti, ozokerite and paraffin wax. These may constitute from 0 to 10%, preferably from 2 to 8% by weight of the product.

The normally solid higher fatty acid amides of alkylolamines are also useful as gelling agents in the antiperspirant stick compositions of the invention. Such amides can be derived by the usual condensation, at elevated temperatures of from 150° to 175° C. of normally solid higher fatty acids, such as palmitic acid, stearic acid, myristic acid and lauric acid, with primary or secondary alkylolamines or hydroxyalkyl amines such as, monoethanoloamine, diethanolamine, n-propanolamine, hydroxyethyl ethylenediamine, glycerolamine, 1-amino-2, 3-propanediol and 2-amino-1,3-propanediol. The condensation products of myristic acid, palmitic acid or stearic acid with monoethanolamine are preferred. The alkylolamides when employed should constitute from 15 to 35% preferably from 20 to 30% by weight of the product.

The gelling agent may also be dibenzyl monosorbitol acetal (DBS), desirably together with a co-solvent such as dihydric and polyhydric alcohols and stabilising agents to prevent acid decomposition of the acetal and subsequent gel breakdown. When employed, DBS should be present in an amount of from 0.5 to 10% preferably 1 to 5% by weight of the product.

Specific examples of co-solvents for DBS include 2-methoxyethanol, 2-ethoxyethanol, ethylene glycol, diethylene glycol, diethylene glycol monomethylether, 1,2-propylene glycol, 1,3-butylene glycol, dipropylene glycol, hexylene glycol, 2,4-dihydroxy-2-methylpentane, polyethylene glycols and mixtures thereof. These should be present in amounts of from 10 to 60%, preferably from 15 to 45% by weight of the product.

Agents suitable for stabilising products according to the invention containing dibenzyl monosorbitol acetal include amines such as methenamine (hexamethylene tetramine), amides such as acetamide,monoethanolamide and cocofatty acid monoethanolamide and basic metallic salts such as zinc oxide, zinc acetate, calcium acetate, zinc carbonate, potassium carbonate, magnesium carbonate and calcium hydroxide. Mixtures of the above organic and inorganic gel stabilising agents are also effective. Ordinarily, the stabilisers will be used in an amount ranging from 0.02 to 10%, preferably from 0.1 to 5% by weight of the product.

Perfume

A perfume can optionally be employed in the product according to the invention. If so, then it should be chosen from any suitable perfume that is compatible with the other ingredients present in the product, and it should also be acceptable to the consumer. A particularly preferred perfume is a deodorant perfume such as one described in GB 2 013 493 (Unilever Limited), which is incorporated herein by reference.

The amount of perfume when employed in the product according to the invention is from 0.01 to 10%, preferably from 0.1 to 5% by weight of the product.

Adjuncts

The product optionally also contain adjuncts other than materials already referred to in the specification, in order to enhance or improve the cosmetic properties of the final product. Examples of other adjuncts include an emollient liquid which is less volatile than isopropanol, such as isopropyl myristate, dipropylene glycol methylether (DOWANOL DPM), propylene glycol, Fluid AP, and dibenzyl phthalate. Further optional adjuncts include talc to impart smooth feel to the stick, titanium dioxide to improve whiteness and antimicrobial agents such as IRGASAN DP 300.

Further adjuncts can include silicone fluids, preferably volatile silicones in an amount of up to 20% by weight of the product.

Particularly preferred volatile silicones are the linear volatile silicones having 2 to 9 silicon atoms such as hexamethyl disiloxane, the cyclic volatile silicones having 3 to 6 silicon atoms such as the tetramer and pentamer, linear non-volatile silicones and mixtures thereof.

The amount by weight of other antiperspirant adjuncts which optionally can be employed in the product according to the invention will generally form the balance of the product.

THE PROCESS

The invention also provides a process for the manufacture of a solid antiperspirant product according to the invention, which process comprises the steps of:
(a) preparing a melt containing:
  (i) from 5 to 35% by weight of a finely divided powder antiperspirant agent;
  (ii) from 15 to 75% by weight of anhydrous ethanol, anhydrous isopropanol or a mixture thereof;
  (iii) from 2 to 15% by weight of an hydrophobically treated clay; and
  (iv) from 0.5 to 35% by weight of a gelling agent; and
(b) pouring the melt into moulds and allowing to solidify to form the solid antiperspirant product.

PRODUCT FORM

The product according to the invention can be fashioned into sticks of usually circular or oval cross-section mounted in a suitable holder fitted with relatively airtight cap, so as to prevent evaporation of alcohol and other volatile ingredients when not in use.

MEASUREMENT OF EFFICACY OF THE ANTIPERSPIRANT PRODUCT

In the following part of this specification references are made to the antiperspirant efficacy of various products. Before giving details of the composition of these products, the test procedure carried out to evaluate their antiperspirant efficacy will first be described. The test procedure, which involves subjecting human volunteers to thermal stress and gravimetric determination of axilla sweat, is summarised as follows:

Subjects: A panel of up to 60 women who use no antiperspirant for the 14 days before the test.
Hot Room: Temperatures 40° C. ±2° C.; relative humidity 40% ±5%.
Products: When testing two products, one being designated the test product and the other the control, the panel is divided into two equal groups. One group receives the test treatment on the left axilla and the control treatment on the right, while the second group receives them the other way round. Alternatively, when comparing two test products against each other and against a control product, then the products are randomly applied to the axillae of the panel subjects, with the proviso that the product applied to left axilla is different from that applied to the right axilla of each subject.

Control Product: This is a placebo deodorant in the form of an aerosol product comprising by weight 25% ethanol, 0.6% isopropyl myristate, 0.3% perfume and 74.1% propellant (1:1 mixture of Propellants 11 & 12).

Product Application: The operator conducting the test applies the test product in a standard manner, so as to deposit an appropriate quantity of product, for example, on average about 300 mg of product to each axilla.

Sweat Collection: Absorbent cotton pads are used to collect the sweat. On entering the hot room, each panellist is subjected to a 40 minute 'warm-up' period, during which no sweat is collected. Sweat is then collected for a 20 minute period and sweat weight determined.

Test Design: Subjects attend daily for 3 consecutive days. They receive one treatment with the products on each of the first three days. Following product application on the third day, the panellist is subjected to a hot room sitting and sweat is collected.

Analysis of Data: The statistical treatment includes an analysis of variance which allows for side effects due to the product and the panellist. The efficacy is calculated from the geometric mean weight of sweat collected from the axillae treated with each product using the formula:

$$\% \text{ sweat reduction} = 100 \frac{(C - T)}{C}$$

where C is the geometric mean sweat weight from the axillae treated with the control product and T is the geometric mean sweat weight from the axillae treated with the test product where a correction has been made for the side effect.

Significance is calculated by applying Student's t-test to the logarithmically transformed weights.

EXAMPLES

Examples 1 to 7 illustrate high efficacy antiperspirant stick formulations according to the invention. These formulations contain the following ingredients:

| | % w/w EXAMPLES | | | | | | |
|---|---|---|---|---|---|---|---|
| | 1 | 2 | 3 | 4 | 5 | 6 | 7 |
| ZAG (Rezal 36GP)[1] | 18 | 18 | 18 | 18 | 18 | 20 | 20 |
| Ethanol (RR, anhydrous) | 42 | 37 | 36 | 36 | 36 | 41 | 35 |
| Volatile silicone 7158[2] | — | 8 | 4 | 4 | — | — | 6 |
| Fluid AP[3] | 5 | 5 | 4 | 4 | — | — | — |
| Bentone 27[4] | 3 | 1 | 5 | — | — | — | — |
| Bentone 38[5] | 3 | 3 | 3 | 8 | 8 | 8 | 8 |
| Castorwax MP80[6] | 4 | 4 | 4 | 4 | — | — | — |
| Alfol 18[7] | 20 | 16 | 18 | 19 | 19 | — | — |
| Synchrowax HRC[8] | — | 3 | 2 | 2 | — | — | — |
| Talc | 4 | 4 | 4 | 4 | — | — | 2 |
| Tiona G[9] | — | — | 1 | — | — | — | — |
| Perfume | 1 | 1 | 1 | 1 | 1 | 1 | 1 |
| Propylene Glycol | — | — | — | — | 18 | 27 | 22 |
| DBS[10] | — | — | — | — | — | 2.5 | 2.5 |
| Zinc Oxide[11] | — | — | — | — | — | 0.5 | 0.5 |
| Empilan CME[12] | — | — | — | — | — | — | 3 |

NOTES
[1]Zirconyl aluminium glycine
[2]Cyclomethicone
[3]Polypropylene glycol ether of butyl alcohol
[4]Stearalkonium Hectorite
[5]Quaternium - 18 Hectorite
[6]Hydroqualid castor oil
[7]Stearyl alcohol
[8]Glyceryl tribehenate
[9]Titanium dioxide whitening agent
[10]Dibenzaldehyde monosorbitol acetal
[11]Zinc oxide to stabilise DBS
[12]Coconut monoethanolamide to stabilise DBS The antiperspirant stick formulations of Examples 1 to 5 were prepared in the following manner:
(i) Bentone was high shear mixed into the liquid components of the formulations (except perfume) for a sufficient period of time to achieve uniform dispersion of the Bentone in the liquids.
(ii) Alfol 18, waxes, talc and Tiona G were added to (i) and the stirred mixture heated to 60° C. for sufficient time to dissolve Alfol 18 and the waxes.
(iii) After cooling to 55° C., ZAG and perfume were uniformly dispersed in the mix.
(iv) Cooling was allowed to continue with constant mixing to 50° C. at which point the melt was poured into stick barrels and allowed to solidify.

The antiperspirant stick formulations of Examples 6 and 7 were prepared in the following manner:
(i) Bentone 38 was high shear mixed into the liquid components of the formulation (except perfume) for a sufficient period of time to achieve uniform dispersion of the Bentone in the liquids.
(ii) DBS, zinc oxide and Empilan CME were added to (i) and the mixture heated to reflux temperature for sufficient time to dissolve the DBS and Empilan CME. The time required to dissolve DBS in ethanol/propylene glycol mixtures is dependent upon the composition of the mixture and this needs to be predetermined by refluxing DBS in the ethanol/propylene glycol in absence of solids until clarity is achieved. Refluxing for 1 hour was sufficient to dissolve DBS in the two examples given here.
(iii) ZAG and perfume were then rapidly mixed into the melt to give a uniform dispersion of these components after which the melt was poured into stick barrels and allowed to solidify.

Hot Room Efficacy Data

The efficacy of the products of Example 4, 5 and 6 were compared in the Hot Room, according to the method described hereinbefore, with 4 commercially available products. The results of this comparative test are shown in Table 1 below:

TABLE 1

| Product | Efficacy: Sweat Weight Reduction (%) |
|---|---|
| Example 4 | 45.2 |

TABLE 1-continued

| Product | Efficacy: Sweat Weight Reduction (%) |
|---|---|
| Example 5 | 53.2 |
| Example 6 | 60.9 |
| P&G SURE (USA) | 31.6 |
| P&G SECRET (USA) | 36.0 |
| ELIDA SURE (UK) | 33.0 |
| GILLETTE RIGHT GUARD (UK) | 37.9 |
| BRISTOL-MYERS ARRID (USA) | 38.0 |
| ARMOUR DIAL (USA) | 32.0 |

It can be seen from an inspection of these results that the product of Examples 4, 5 and 6 demonstrably reduced sweat by amounts which by far exceeded that of each of the commercial products with which they were compared.

We claim:

1. A solid antiperspirant product suitable for topical application to the skin, which comprises from 5 to 35% by weight of an antiperspirant agent in the form of fine particles dispersed in a solid matrix comprising:
    (i) from 15 to 75% by weight of the product of a substantially anhydrous alcohol selected from the group consisting of ethanol, isopropanol or a mixture thereof;
    (ii) from 2 to 15% weight of the product of a hydrophobically-treated clay suspending agent;
    (iii) from 0.5% to 35% by weight of a gelling agent; provided that the weight ratio of the suspending agent to the anhydrous alcohol is from 1:3 to 1:15.

2. The antiperspirant product of claim 1, wherein the antiperspirant agent has a mean particle size of not greater than 100μ.

3. The antiperspirant product of claim 1, wherein the antiperspirant agent is selected from the group consisting of aluminium salts, zironcium salts and mixtures thereof.

4. The antiperspirant product of claim 1, wherein the antiperspirant active agent is an aluminium chlorohydrate.

5. An antiperspirant product according to claim 1, in which the antiperspirant agent is chosen from aluminium zirconium trichlorohydrex-GLY, aluminium zirconium tetrachlorohydrex-GLY and mixtures thereof.

6. The antiperspirant product of claim 1, wherein the hydrophobically-treated clay comprises a smectite clay.

7. The antiperspirant product of claim 6, wherein the hydrophobically-treated clay is quaternium 18 hectorite.

8. An antiperspirant product according to claim 1 in which the weight ratio of suspending agent to anhydrous alcohol is from 1:4 to 1:10.

9. An antiperspirant product according to claim 1 which further comprises a perfume.

10. A solid antiperspirant product of claim 1 further comprising an effective amount of at least one antiperspirant adjunct selected from the group consisting of perfume, emollient liquids less volatile than isopropanol, talc, titanium dioxide, antimicrobial agents and volatile silicone fluids.

11. A solid antiperspirant product suitable for topical application to the skin, which comprises 5 to 35% by weight of an antiperspirant agent in the form of fine particles dispersed in a solid matrix comprising:
    (i) from 15 to 75% by weight of the product of a substantially anhydrous alcohol selected from the group consisting of ethanol, isopropanol or a mixture thereof;
    (ii) from 2 to 15% by weight of the product of a hydrophobically-treated clay suspending agent obtained by reacting a clay in a cation exchange system with an amine; and
    (iii) from 0.5% to 35% by weight of a gelling agent; provided that the weight ratio of the suspending agent to the anhydrous alcohol is from 1:3 to 1:15.

12. An antiperspirant product according to claim 11, in which the hydrophobically-treated clay is a stearalkonium hectorite.

13. An antiperspirant product according to claim 11, in which the hydrophobically-treated clay is quaternium 18 hectorite.

14. An antiperspirant product according to claim 11, in which the hydrophobically-treated clay is quaternium 18 bentonite.

15. A process for the manufacture of a solid antiperspirant product, which process comprises the steps of:
    (a) preparing a melt containing:
        (i) from 5 to 35% by weight of a finely divided powder antiperspirant agent;
        (ii) from 15 to 75% by weight of a substantially anhydrous alcohol selected from the group consisting of ethanol, isopropanol or a mixture thereof;
        (iii) from 2 to 15% by weight of an hydrophobically-treated clay; and
        (iv) from 0.5 to 35% by weight of gelling agent and;
    (b) pouring the melt into moulds and allowing to solidify to form the solid antiperspirant product.

16. The process of claim 15 wherein the melt additionally contains at least one antiperspirant adjunct selected from the group consisting of perfume, emollient liquids less volatile then isopropanol, talc, titanium dioxide, antimicrobial agents and volatile silicone fluids.

* * * * *